(12) United States Patent
Atiya et al.

(10) Patent No.: US 12,402,988 B2
(45) Date of Patent: Sep. 2, 2025

(54) MULTIMODAL INTRAORAL SCANNING

(71) Applicant: ALIGN TECHNOLOGY, INC., San Jose, CA (US)

(72) Inventors: Yossef Atiya, Modiin-Maccabim-Reut (IL); Maayan Moshe, Ramat Hasharon (IL)

(73) Assignee: Align Technology, Inc., San Jose, CA (US)

( * ) Notice: Subject to any disclaimer, the term of this patent is extended or adjusted under 35 U.S.C. 154(b) by 385 days.

(21) Appl. No.: 17/813,555

(22) Filed: Jul. 19, 2022

(65) Prior Publication Data

US 2023/0021695 A1 Jan. 26, 2023

Related U.S. Application Data

(60) Provisional application No. 63/203,404, filed on Jul. 21, 2021.

(51) Int. Cl.
| | | |
|---|---|---|
| A61C 9/00 | (2006.01) |
| A61B 1/00 | (2006.01) |
| A61B 5/00 | (2006.01) |
| A61C 7/00 | (2006.01) |
| A61C 13/34 | (2006.01) |

(52) U.S. Cl.
CPC .......... *A61C 9/006* (2013.01); *A61B 1/00172* (2013.01); *A61B 5/0066* (2013.01); *A61C 7/002* (2013.01); *A61C 13/34* (2013.01)

(58) Field of Classification Search
None
See application file for complete search history.

(56) References Cited

U.S. PATENT DOCUMENTS

| | | | |
|---|---|---|---|
| 6,099,314 | A | 8/2000 | Kopelman et al. |
| 6,334,772 | B1 | 1/2002 | Taub et al. |
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |
| 6,979,196 | B2 | 12/2005 | Nikolskiy et al. |
| 7,030,383 | B2 | 4/2006 | Babayoff et al. |
| 7,202,466 | B2 | 4/2007 | Babayoff et al. |
| 7,255,558 | B2 | 8/2007 | Babayoff et al. |
| 7,286,954 | B2 | 10/2007 | Kopelman et al. |
| 7,319,529 | B2 | 1/2008 | Babayoff |
| 7,373,286 | B2 | 5/2008 | Nikolskiy et al. |
| 7,507,088 | B2 | 3/2009 | Taub et al. |
| 7,545,372 | B2 | 6/2009 | Kopelman et al. |
| 7,698,068 | B2 | 4/2010 | Babayoff |
| 7,916,911 | B2 | 3/2011 | Kaza et al. |

(Continued)

*Primary Examiner* — Kaitlin A Retallick
(74) *Attorney, Agent, or Firm* — FisherBroyles, LLP

(57) ABSTRACT

A method of multimodal scanning may include generating surface scan data of an intraoral structured using structured light. The method may include generating volumetric scan data of an internal structure of the intraoral structure with OCT scanning. The OCT scan data may be aligned with the surface scan data. A three-dimensional volumetric model of the patient's dentition may be generated based on the aligned OCT scan data and the surface scan data.

19 Claims, 10 Drawing Sheets

(56) References Cited

U.S. PATENT DOCUMENTS

| | | |
|---|---|---|
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 * | 11/2018 | Elbaz ................ G06T 7/75 |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 * | 12/2019 | Elbaz ................ A61B 1/046 |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,888,400 B2 * | 1/2021 | Elbaz ................ A61B 1/00009 |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 11,096,765 B2 * | 8/2021 | Atiya ................ A61B 1/00172 |
| 11,238,586 B2 | 2/2022 | Minchenkov et al. |
| 11,357,603 B2 * | 6/2022 | Elbaz ................ A61B 1/00045 |
| 11,367,192 B2 | 6/2022 | Kopelman et al. |
| 11,628,046 B2 * | 4/2023 | Elbaz ................ A61B 5/1079 433/29 |
| 11,633,268 B2 * | 4/2023 | Moalem ................ G06T 15/08 433/203.1 |
| 11,826,225 B2 * | 11/2023 | Saphier ............... G02B 27/4227 |
| 11,883,259 B2 * | 1/2024 | Elbaz ................ A61B 1/00045 |
| 11,896,461 B2 * | 2/2024 | Saphier ............... G02B 27/4227 |
| 12,042,124 B2 * | 7/2024 | Rudnitsky ........... A61B 1/0638 |
| 2009/0185191 A1 * | 7/2009 | Boppart ............... A61B 5/6852 356/479 |
| 2018/0027159 A1 * | 1/2018 | Dillon ................ A61B 5/0088 348/66 |
| 2018/0085002 A1 * | 3/2018 | Glinec ................ A61C 9/0073 |
| 2019/0029784 A1 | 1/2019 | Moalem et al. |
| 2019/0258690 A1 * | 8/2019 | Elbaz ................ H04N 13/221 |
| 2019/0269485 A1 * | 9/2019 | Elbaz ................ A61B 5/1079 |
| 2019/0388193 A1 | 12/2019 | Saphier et al. |
| 2020/0022584 A1 * | 1/2020 | Kopelman ........... A61B 5/0088 |
| 2020/0281702 A1 | 9/2020 | Kopelman et al. |
| 2020/0315434 A1 | 10/2020 | Kopelman et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0068779 A1 * | 3/2021 | Lechner ................ A61C 19/04 |
| 2021/0121049 A1 | 4/2021 | Rudnitsky et al. |
| 2021/0128281 A1 * | 5/2021 | Peleg ................ A61B 1/24 |
| 2021/0137653 A1 | 5/2021 | Saphier et al. |
| 2021/0196152 A1 | 7/2021 | Saphier et al. |
| 2022/0051406 A1 * | 2/2022 | Jang ................ A61C 9/0046 |
| 2022/0265400 A1 * | 8/2022 | Jeong ................ A61C 13/0004 |
| 2022/0354623 A1 * | 11/2022 | Ciriello ................ A61B 1/24 |
| 2023/0000600 A1 * | 1/2023 | Wong ................ A61C 9/0046 |
| 2023/0240819 A1 * | 8/2023 | Elbaz ................ A61B 1/00016 433/29 |
| 2024/0036448 A1 * | 2/2024 | Atiya ................ G03B 21/2013 |
| 2024/0163413 A1 * | 5/2024 | Saphier ............... G01B 11/2545 |
| 2024/0197448 A1 * | 6/2024 | Saphier ................ A61C 9/006 |

\* cited by examiner

MULTIMODAL INTRAORAL SCANNING

RELATED APPLICATIONS

This application claims the benefit under 35 U.S.C. § 119(e) of U.S. Provisional Patent Application No. 63/203,404, filed Jul. 21, 2021, which is incorporated, in its entirety, by this reference.

BACKGROUND

The present disclosure is generally related to scanning and generating models of a patient's dentition.

Dental treatments may involve procedures for repositioning misaligned teeth and changing bite configurations for improved cosmetic appearance and/or dental function. Repositioning can be accomplished, for example, by applying controlled forces to one or more teeth over a period of time. A tooth movement in response to the forces applied depends on both the shape of the exposed crown and the shape of sub gingival tissue such as the tooth's root. Existing scanning systems and methods are less than ideal in at least some respects. For example, existing scanning systems do not acquire a sub gingival tooth structure in a way that can be used in orthodontic treatment planning processes.

Restorative treatment planning is a process by which teeth crowns, bridges, implants, and other prosthetics are designed and used in order to restore the patient's dentition. In the restorative treatment planning process for the crown or a bridge, for example, a location and shape of a margin line of a prepared tooth is used in order to fabricate a crown or bridge. The margin line is typically located beneath the gingiva of a patient in the process of exposing the margin line in order to scan it with an intraoral scanner, such as a structured light scanner may be a painful and time-consuming process that involves packing the gingiva to push it away from the patient's tooth and then releasing the packing and quickly scanning the patient's tooth margin line before the gingiva collapses over the margin line. This process is less than ideal because it is painful to the patient and usually involves local anesthetic.

Current scanning systems also fail to detect caries, periodontitis, and cancers.

In light of the above, improved devices and methods that overcome at least some of the above limitations of the prior devices and methods would be helpful.

SUMMARY

Embodiments of the present disclosure provide improved intraoral scanning systems and methods provide more accurate models of the patient's teeth through a multimodal scanning and multimodal scanners.

In some embodiments, a method of multimodal scanning may include generating surface scan data of an intraoral structure using an intraoral scanner. The method may include generating volumetric scan data of an internal structure of the intraoral structure with OCT scanning, including subsurface volumetric scan data. The OCT scan data may be aligned with the surface scan data. A three-dimensional volumetric model of the patient's dentition may be generated based on the aligned OCT scan data and the surface scan data.

In some embodiments, a multimodal scanning system for scanning an intraoral object may include an intraoral scanning wand having a distal end and a proximal end. In some embodiments, a probe may be located at a distal end of the wand. A structured light projector may be located at a proximal end of the probe and configured to project light out of a distal end of the probe. An OCT scanning system configured to project light out of the distal end of the probe.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The methods, apparatus, and systems disclosed herein are well suited for combination with prior devices such as intraoral scanners, for example the iTero system commercially available from Align Technology, Inc.

The presently disclosed methods and systems are well suited for combination with prior approaches to scanning intraoral structures, such as with generating three-dimensional models of a patient's dentition.

Figure 1A:
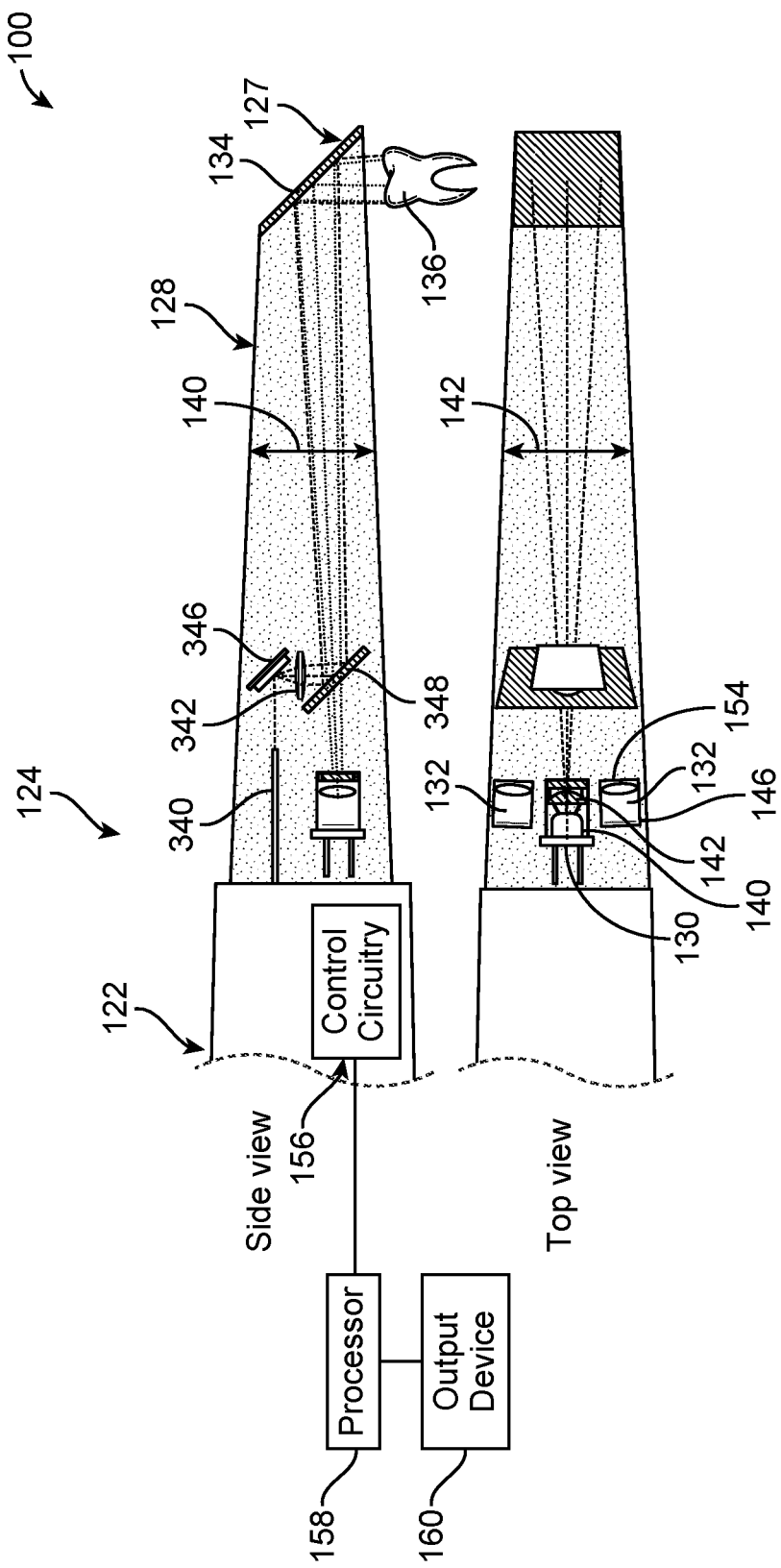
FIG. 1A shows a multimodal scanner, in accordance with some embodiments.
Figure 1B:
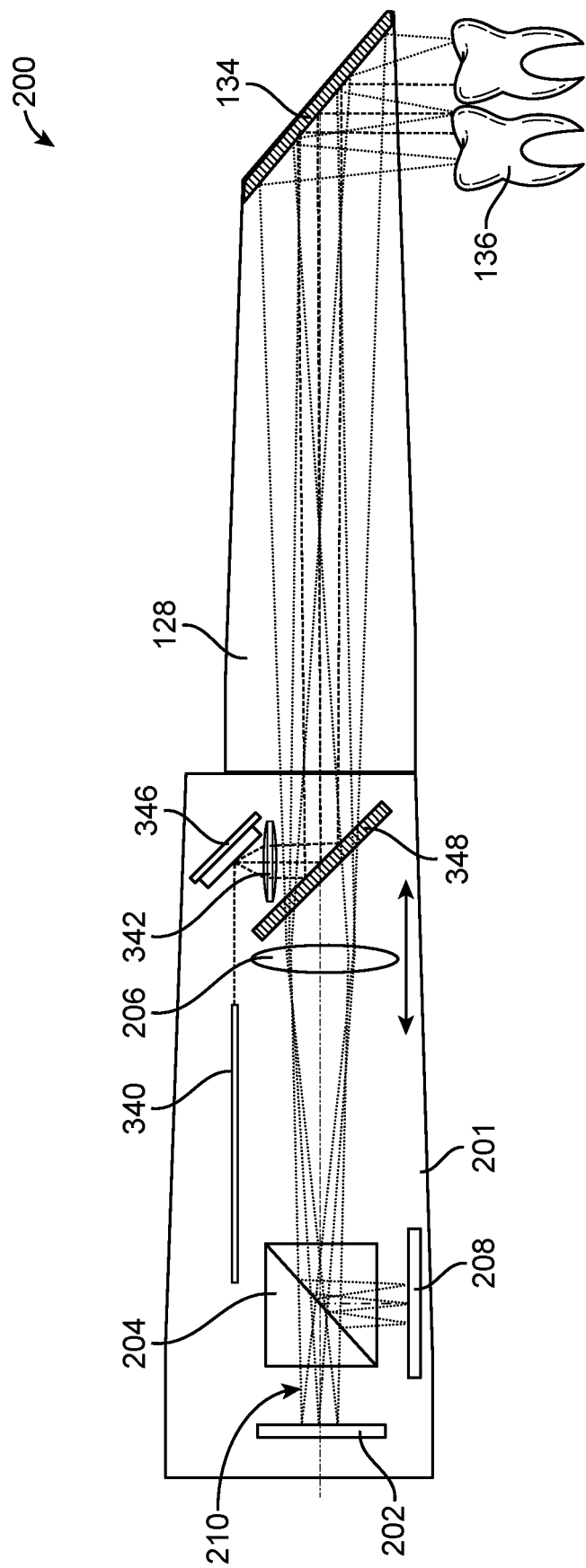
FIG. 1B shows a multimodal scanner, in accordance with some embodiments.
Figure 2:
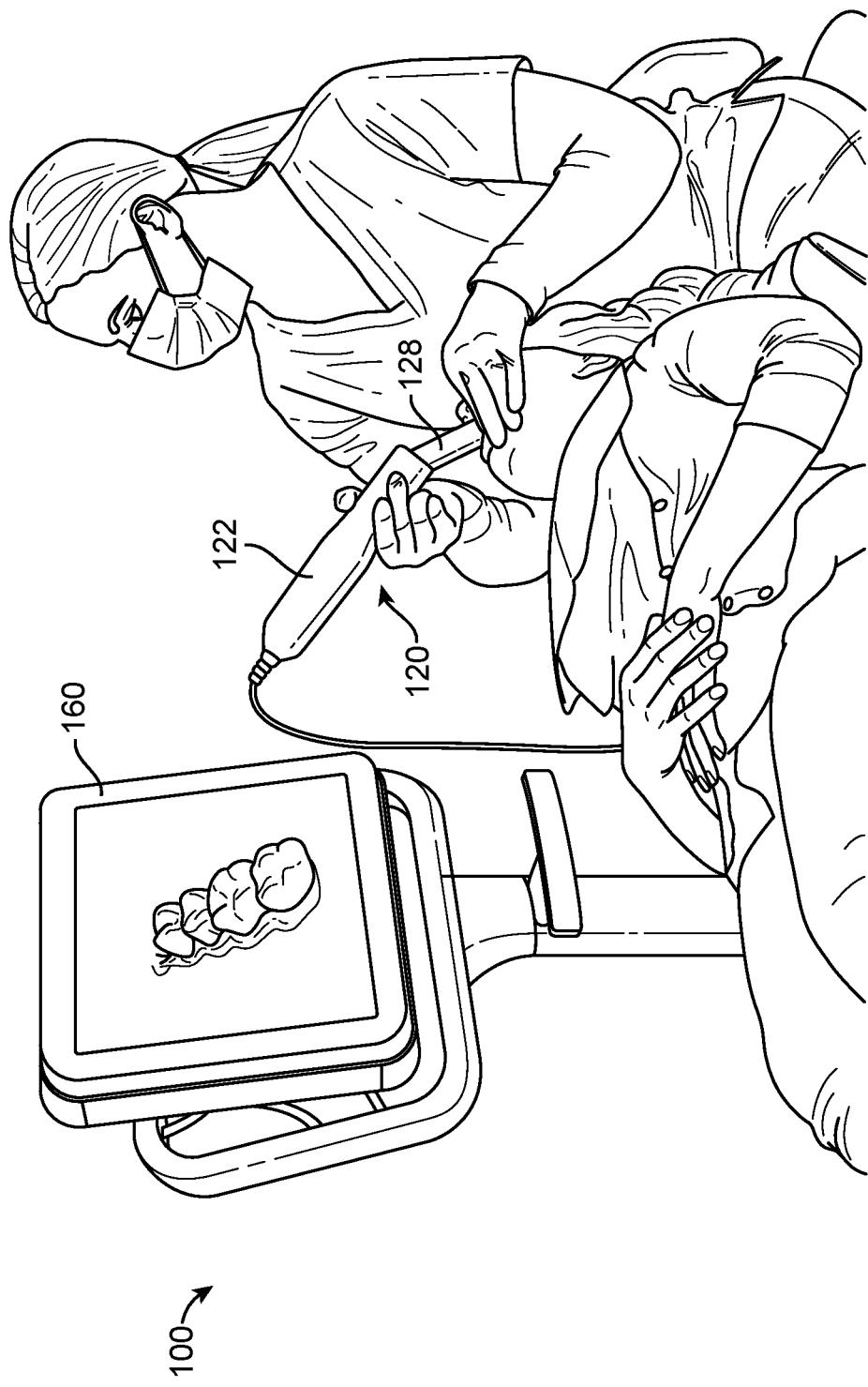
FIG. 2 shows a multimodal scanning system, in accordance with some embodiments.

Reference is now made to FIGS. 1 and 2, which are a schematic illustrations of an intraoral scanning system 100, in accordance with some embodiments of the present invention. intraoral scanning system 100 comprises an elongate handheld wand 122 that has a probe 128 at distal end of the handheld wand 122. Probe 128 has a distal end 127 and a proximal end 124. As used herein, the proximal end of the handheld wand is the end of the handheld wand that is closest to a user's hand when the user is holding the handheld wand in a ready-for-use position and the distal end of the handheld wand is defined as the end of the handheld wand that is farthest from the user's hand when the user is holding the handheld wand in a ready-for-use position.

In some embodiments, a structured light projector 130 is disposed in proximal end 124 of probe 128, one or more imaging cameras 132 are disposed in proximal end 124 of probe 128, and a mirror 134 is disposed in distal end 127 of probe 128. Structured light projector 130 and imaging camera 132 are positioned to face mirror 134, and mirror 134 is positioned to reflect light from structured light projector 130 directly onto an object 136 being scanned and reflect light from object 136 being scanned into imaging camera 132.

Structured light projector 130 includes a light source 140. In some embodiments, structured light projector 130 may have a field of illumination of at least 6 degrees. In some embodiments, the field of illumination may be between about 6 degrees and about 30 degrees. In some embodiments, the field of illumination may be less than about 30 degrees. In some applications, structured light projector 130 focuses light from light source 140 at a projector focal plane that may be located external to the probe and at an object to be scanned 136. In some embodiments, the focal plane may be at least 30 mm from the light source 140. In some embodiments, the focal plane may be between 30 mm and 140 mm from the light source 140. In some embodiments, the light source may be less than 140 mm from light source 140. Structured light projector 130 may have a pattern generator 142 that is disposed in the optical path between light source 140 and the projector focal plane. Pattern generator 142 generates a structured light pattern at projector focal plane 138 when light source 140 is activated to transmit light through pattern generator 142.

Imaging cameras 132 may have a field of view of at least 6 degrees. In some embodiments, the field of view may be between about 6 degrees and about 30 degrees. In some embodiments, the field of view may be less than about 30 degrees. Imaging camera or cameras 132 may focus at a camera focal plane that may be located at least 30 mm from the imaging camera 132. In some embodiments, the focal plane may be between 30 mm and 140 mm from the imaging camera 132. Imaging camera 132 has a imaging camera sensor 146 that comprises an image sensor comprising an array of pixels, e.g., a CMOS image sensor. Imaging camera 132 additionally may have an objective lens 154 disposed in front of imaging camera sensor 148 that forms an image of object 136 being scanned onto imaging camera sensor 146.

Intraoral scanner 100 may include control circuitry 156 that drives structured light projector 130 to project a structured light pattern onto object 136 outside handheld wand 122 and drives imaging camera 132 to capture an image that results from the structured light pattern reflecting off object 136. The structured imaging contains information about the intensity of the structured light pattern reflecting off object 136 and the direction of the light rays. The imaging also contains information about phase-encoded depth via which the scene depth can be estimated from different directions. Using information from the captured imaging, a computer processor 158 may reconstruct a three-dimensional image of the surface of object 136 and may output the image to an output device 160, e.g., a monitor. It is noted that computer processor 158 is shown herein, by way of illustration and not limitation, to be outside of handheld wand 122. In some embodiments, computer processor 158 may be disposed within handheld wand 122.

In some embodiments, object 136 being scanned is at least one tooth inside a subject's mouth. Imaging camera 132 in intraoral scanner 120 may capture the imaging from the structured light pattern reflecting off the tooth without the presence of an opaque or other powder on the tooth, enabling a simpler digital intraoral scanning experience.

The structured light scanning system may generate point clouds representing the three-dimensional surface of the object 136 being scanned. The structured light service may generate up to 60 frames per second of point cloud data that may be used to generate a three-dimensional model of the surface of the object 136 being scanned. In some embodiments, the point cloud data may be used to determine the position and orientation of the scanning wand with respect to the intraoral structure of the object 136 being scanned.

In some embodiments, the structured light scanning system may also capture the color of the surfaces of the object 136. For example, in some embodiments the structured light source may be a white light source and the imaging camera 132 may record the color of the surface of the object 136 based on the light reflected from the object.

Figure 3:
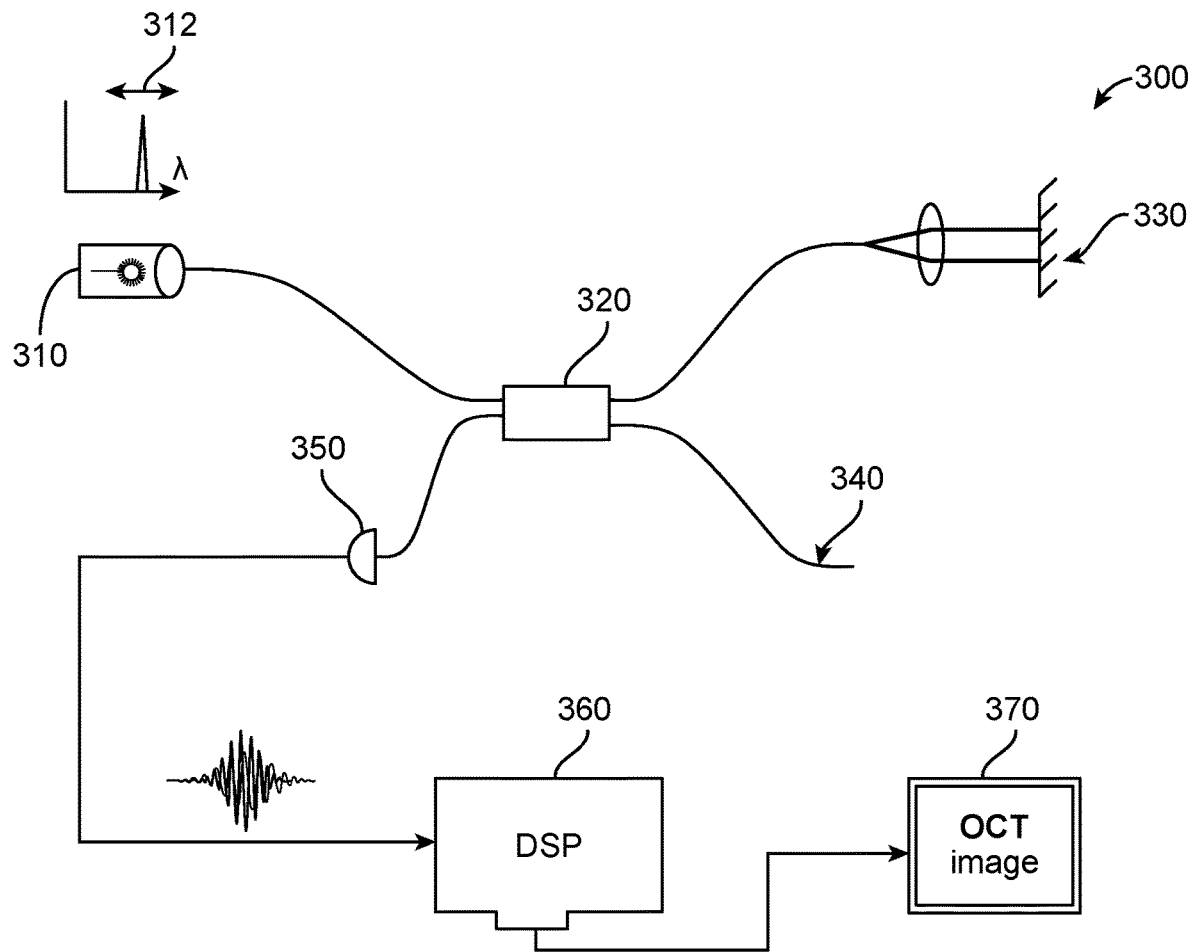
FIG. 3 shows an OCT scanning system of a multimodal scanner, such as a swept source OCT scanning system (SS-OCT), in accordance with some embodiments.

With reference to FIGS. 1-3, the intraoral scanning system 100 may include an optical coherence tomography (OCT) scanning system. Optical coherence tomography is an imaging technique that uses low-coherence light to capture high resolution (micrometer-resolution) data from within optical scattering material, such as a patient's intraoral structures, including the teeth and gingiva. In an OCT imaging system light is backscattered from the tissue, such as the teeth or gingiva and the backscattered light is compared to that of a reference beam of light. The superposition of both waves creates an interference pattern that's used to measure the light echoes versus the depth profile of the intraoral structure.

The OCT system 300 described herein may use a swept source OCT process in which light of multiple varying frequencies is projected into the intra oral structure and the resulting interference patterns are processed in the frequency domain, for example, by processing the interference patters after conducting a Fourier transformation, which allows simultaneous measurement of all light echo interference patterns. The OCT system 300 may include a swept source light source 310, a beam splitter 320, a reference mirror 330, and object armed 340, a photodetector 350, and a digital signal processor 360.

The swept-source light source 310 may be a laser light source that may emit light at the plurality of wavelengths centered at 1310 nm. In some embodiments, the light source may be centered at 850 nm. In some embodiments, the laser light source may emit light at a wavelength centered about a wavelength between 850 nm and 1600 nm. The laser light source may emit light that sweeps across a narrow band 312 of wavelengths around its center wavelength, such as +/−10 to +/−20 nm. In some embodiments, the sweep bandwidth may be between 40 nm and 250 nm above and below the center bandwidth. In some embodiments, the photo detector may be one or more of the light sensors 132.

Light from the light source 310 may be projected onto a beam splitter 320. The beam splitter 320 splits the incoming light from the swept source light source 310 and sends a first portion of light towards a reference mirror 330 and a second portion of light to the object armed 340. The light sent towards the reference mirror 330 is reflected off the reference mirror 330 and back through the beam splitter and onto the photodetector 350. The light sent towards the object arm is transmitted to the object 136. The light travels into the object 136 and is reflected off the internal, subsurface, structures of the intraoral structure being scanned. The light reflected from the intraoral structure travels through the beam splitter and onto the photodetector 350.

The reference mirror 330 may be located a known distance from the beam splitter 320 and/or the swept source 310. The object 136 that is being scanned may be located at an unknown distance from the beam splitter and or the swept source, however interference patterns between the light from the reference mirror and the light from the object 136 may be recorded by the photodetector, such as one or more of the light sources 132.

The digital signal processor 360 may process the recorded interference patterns and based on the recorded interference patterns determine the depth from which the light is reflected off the object 136. The intensity of the reflected light from a given depth may relate to the density of the material and internal structures within the intraoral structure being scanned, such as within the tooth. Based on this data an OCT image 370 of the internal structures of the intraoral structure may be determined. The image may be an optical cross-section of the subsurface tooth structures.

The OCT light source may have a field of illumination that is less than the field of illumination of the structured light projector 130 and the field of view of the cameras 132. In some embodiments, the field of illumination of the OCT light source may be less than 1 degree. In some embodiments, the field of illumination may be less than 0.1 degrees. In order for the OCT scanner to gather data in a field that is greater than the field of illumination of the OCT light source more, a scanning mirror 346 and scanning lens 342 may be used to scan the OTC light source's field of illumination over a greater field.

Figure 4:
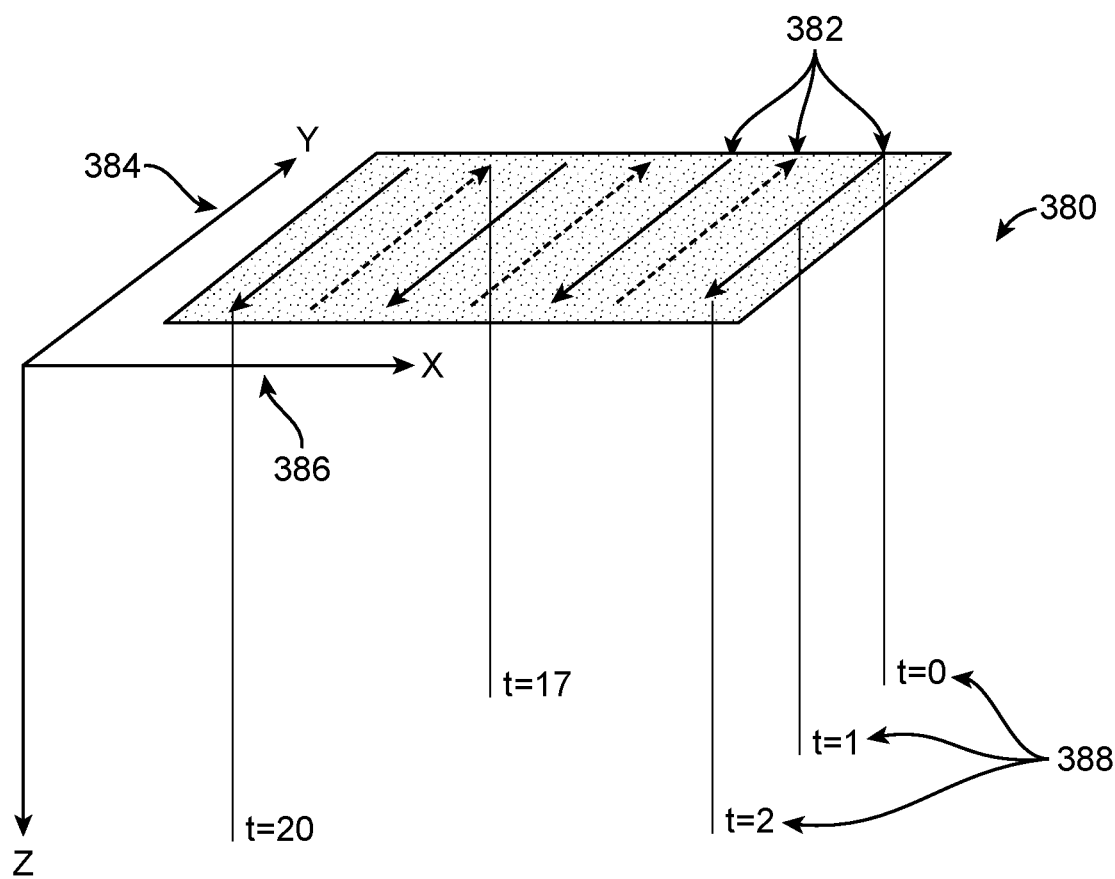
FIG. 4 shows a scan pattern for an OCT scanning system, in accordance with some embodiments.

With reference to FIG. 4, the scanning mirror 346 and scanning lens 342 may work together to scan the OCT light sources field of illumination a scan pattern 380. The scan pattern 380 scan the field of view back and forth along paths 382 that are parallel to a first axis 384, such as an x-axis, and shift each path along a second axis 386 that is perpendicular to the first axis 384, such as a y-axis. By using such a scan pattern 380, the OCT light source illuminate a larger two-dimensional field of illumination. The location of the OCT light source field of illumination may be recorded for each time period 388 of a scan. The scan pattern 380 may be repeated during the scanning process. In some embodiments, scan pattern 380 scans the OCT light source field of illumination over a field that is the same as the field of illumination or field of view of the structured light projector 130 or the cameras 132, respectively. In some embodiments, the scan pattern 380 scans the OCT light source field of illumination over a field that is less than the field of illumination or field of view of the structured light projector 130 or the cameras 132, respectively. In some embodiments, the reflected light from the intraoral object 136 is polarized, such as by a polarizing filter, before reaching the imaging sensor 132.

In some embodiments, the OCT scanning system 300 may generate depth scans that penetrate into object 136 a distance of 1 to 3 mm. In some embodiments, the OCT scanning system may generate depth scans that penetrate into the object a distance of up to 4 mm.

Intraoral scanner 100 may include control circuitry 156 that drives the OCT scanning system 300 to project the light from the OCT light source in the scan pattern onto object 136 outside handheld wand 122, and drives camera 132 to capture a imaging that results from the OCT light scored scan pattern reflecting off object 136. The reflected light contains information about the intensity and wavelength of the light reflected off the internal structures of the object 136. Using information from the captured light, a computer processor 158, such as digital signal processor 360, may reconstruct a three-dimensional image of the internal structure of object 136 and may output the image to an output device 160, e.g., a monitor. It is noted that computer processor 158 is shown herein, by way of illustration and not limitation, to be outside of handheld wand 122. In some embodiments, computer processor 158 may be disposed within handheld wand 122.

The OCT scanning system 300 may collect data over the scan pattern 380 at a rate that is less than the rate at which the structured light system generates a three-dimensional point clouds. For example, in some embodiments the OCT scanning system may collect data over the scan pattern at a rate of one scan pattern per second. In some embodiments, the OCT scanning system 300 may collect data over the field of view of the image sensors 132 at a rate of greater than one scan per second, such as about 20 scans per second. In some embodiments, the rate may be between 10 and 40 volume scans per second.

In some embodiments, the digital signal processor 360 may correct for diffraction effects caused by the different wavelengths of light traveling through the intraoral structure of the object 136. In some embodiments, for example with caries detection, the diffraction effects may be less than 100 μm and may be ignored. In some embodiments, for example margin line scanning, the diffraction effects may be corrected.

In some embodiments, the intraoral scanning system 100 may include a near infrared (NIR) scanning system. The near infrared scanning system may include a near infrared light source and a camera. The near infrared light source may be a light source such as the light source 140 of the structured light projector 130 In the camera may be the camera 132. In some embodiments, the in near infrared scanning system, the structured light system, in the OCT scanning system 300 more coaxial to each other.

The control circuitry 156 may also drive the near infrared scanning system and coordinate the illumination and recording of the near infrared light with that of the structured light and the OCT light.

When structured light projector 130 and imaging camera 132, and the object arm 340 are disposed in proximal end 124 of probe 128, the size of probe 128 is limited by the angle at which mirror 134 is placed. In some embodiments, a height 140 of probe 128 is less than 17 mm, and a width 143 of probe 128 is less than 22 mm, height 140 and width 143 defining a plane that is perpendicular to a longitudinal axis of handheld wand 122. The height 140 of probe 128 is measured from a lower surface (scanning surface), through which reflected light from object 136 being scanned enters probe 128, to an upper surface opposite the lower surface. In some embodiments, the height 140 is between 14-17 mm. In some embodiments, the width 143 is between 18-22 mm.

FIG. 1B shows a confocal scanning system integrated with an OCT scanning system in a single handheld intraoral scanner 200. The confocal system includes a patterned light source 202, a beam splitter 204, and focusing and imaging optics 206, and a color image sensor 208 located within the scanner body 201. During use, the patterned light source 202 generates a 2D light pattern such as an 2D array of light beams 210. The light beams pass through a beam splitter 204 and then through focusing and imaging optics 206. The focusing and imaging optics 206 may include one or more lenses to confocally focus the light beams on the object 136. The light beams then pass through a dichroic mirror 348 and are reflected off of the mirror 134 before illuminating the object 136. Light from the 2D array of light beams is reflected off of the object 134 back into the scanner 200. The reflect light reflects off of the mirror 134, passes through the dichroic mirror 348 and the focusing optics 206 before being reflected by the beam splitter into a color image sensor. The image sensor records an images of the light data for each part of the object. The images are then processed to generate depth data, such as point clouds, for the surface of the object 136. Many frames of depth data are then stitched together to generate a 3D model of the object. The OCT entry point into the light path may be preferably placed after the last confocal optical element to avoid the need for ultra-wide spectral bandwidth optics. The probe may be hollow and free of refractive optical elements for the same reason. The OCT scanning elements of scanner 200 may include some or all of the OCT devices and system described herein, such as with respect to FIGS. 1-3. The object arm 340, the scanning lens 342, and the scanning mirror 346, along with the other elements of the OCT scanning system of the intraoral scanner 200 may be the same or similar to and my operate in the same or similar way as the OCT system shown and described with respect to FIGS. 1-4.

The surface scanner, such as the confocal system or the structured light system, operate in the visible wavelength band while OCT operates in the near infrared wavelength band. This enables the use of dichroic filter or mirror 348 to combine and separate between these two wavelength bands, thus allowing the freedom to implement each channel independently.

As discussed herein, the structured light scanning system or confocal scanning system collects point cloud data of the surface of the object 136 at a rate that is much faster than the rate at which the OCT scanning system collects data for the internal structure of the object 136 over the same field of view. For example, a structure light scanning system may scan the field of view at a rate of 2 to 10 times the rate that the OCT scanning system collects data over a field of view. In some embodiments, the generation of a point cloud for a given wand location may occur at a speed at which the relative movement of the wand during the scan over the field of view may be ignored. However, in some embodiments, the movement of the scanning wand during the OCT scanning of a scanned pattern may be accounted for in order to build an accurate model of the internal structure of the object 136. For example, with reference to FIG. 4, t=1 the scanning wand may be at a first location in first orientation while at t=2 the scanning wand may be at a second location in a second orientation. If these changes in location and orientation are not accounted for the data processing than the three-dimensional model of the internal structure of the object 136 may be inaccurate.

Figure 5:
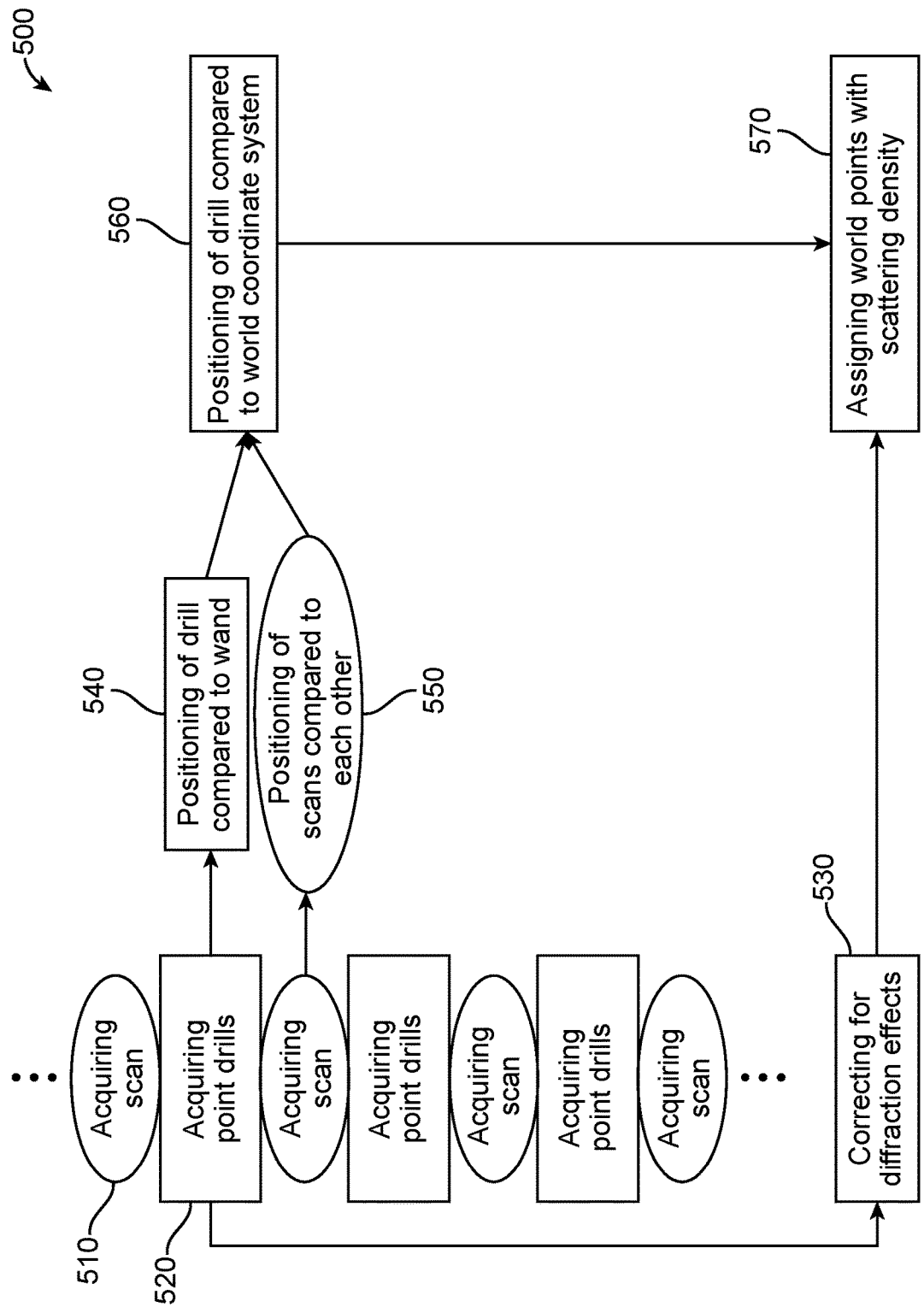
FIG. 5 a method of fusing OCT scan data with structured light scan data, in accordance with some embodiments.

In some embodiments, the structured light data or confocal data may be used in order to determine the appropriate location within the three-dimensional model in which to place the OCT scanning data. FIG. 5 depicts an embodiment of a method 500 for registering or fusing the OCT scan data with the structured light scan or confocal scan surface data in order to create a three-dimensional model of the external surface and internal structure of the patient's intraoral structure.

The method 500 includes a plurality of repeated steps that are used in order to align the OCT scan data with the structured light data or confocal data and/or the near infrared data. At block 510 one or more point clouds are generated using the structured light or confocal system. The point clouds represent the location of the surface of the object 136 over the field of view of the camera 132 and/or the field of illumination of the structured light projector 130 or confocal system. The time at which each of the point clouds are generated may be recorded. At block 520 the OCT scanning system generates point drills through the depth of the internal structure of the object 136 in the scan pattern 380, the position of the OCT light source field of illumination within the scan pattern may be recorded. As depicted in FIG. 5, the generation of the point clouds at block 510 and the generation of the OCT scan data at block 520 may overlap.

At block 540, the location of the OCT light source field of illumination within the scan pattern at a given time may be compared to the three-dimensional point cloud generated at the same time in order to determine the position of the point or depth drill compared to the position of the wand at that time. In some embodiments, an acquired point drill may occur at a time between the generation two point clouds. In such an embodiment, interpolation between the position of the wand during the generation of the first of the two point clouds and the position of the wand during the second of the two point clouds may be used in order to determine the position of the wand during the generation of an acquired point drill. The interpolation between two point clouds may assume a constant speed of movement of the one between the capture of the first and second point clapped. The At block 550, after determining the position of the drill with respect to the position of the wand, the OCT scan data acquired during the point drill may be positioned within a three-dimensional model with respect to the three-dimensional surface data of the object 136. Over the course of a scanning session, the actions at blocks 510, 520, 540, 550 may be repeated and during each iteration, newly acquired surface and internal structure data may be added to the overall three-dimensional model of the object 136. For example, at block 560 the positioning of the OCT scan data and/or the point cloud data may be oriented with respect to a global coordinate system and then at block 570 the OCT scan data and or the point cloud data may be assigned location within the global coordinate system and integrated into the overall model of the object 136. In some embodiments, at block 530 the acquired point drill data may be corrected for diffraction effects. The correction may occur before block 540 at which the OCT data's position with respect to the wand. The overall model of the object 136 generated by the fusion of the surface scan data and the subsurface scan data such as the internal density and morphology tooth results in a comprehensive and position accurate volumetric map of the oral cavity. The volumetric map may be displayed to the user and overlaid over and inside the jock topography.

In some embodiments one or more indications may be provided on the display based on the volumetric map potent densities of the object 136. The indications may include the locations of oral lesions such as caries, periodontal disease, and oral cancer. In some embodiments, the indications may include subsurface or sub gingival structures such as the location and shape of a sub gingival margin line of a prepared tooth. In some embodiments, the oral lesions may be color-coded based on their type and the level of risk they may represent. In some embodiments, machine learning may be used to analyze subsurface scan data to identify the lesions, margin lines, or to segment the volumetric data between hard tissue, such as a tooth and soft tissue, such as the gingiva. Various features and methods of identifying oral lesions with machine learning are described, for example, in U.S. patent application Ser. No. 63/124,721, titled "NON-INVASIVE MULTIMODAL ORAL ASSESSMENT AND DISEASE DIAGNOSES APPARATUS AND METHOD" which is herein incorporated by reference in its entirety.

Figure 6:
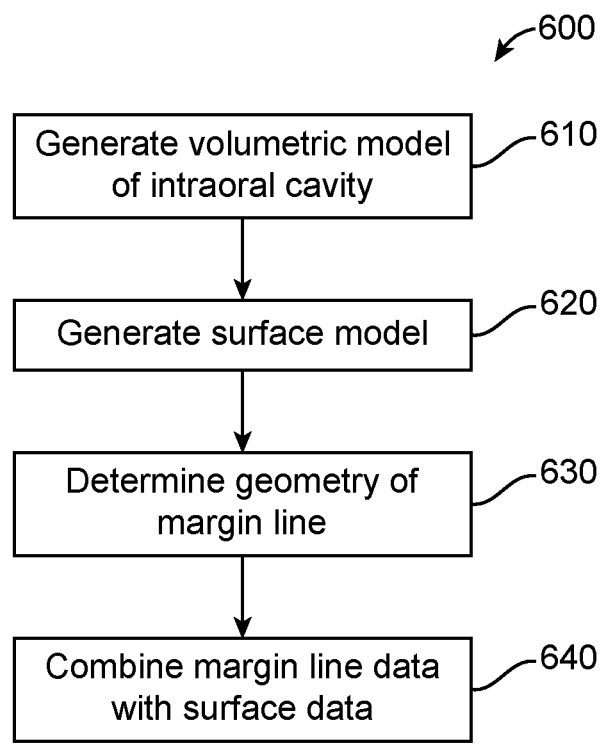
FIG. 6 shows a method of using multimodal scanning systems and methods in restorative treatment planning, in accordance with some embodiments.

With reference to FIG. 6, a method 600 of using a multimodal scanner in restorative treatment planning is shown. Restorative treatment planning is a process by which teeth crowns, bridges, implants, and other prosthetics are designed and used in order to restore the patient's dentition. In the restorative treatment planning process for the crown or a bridge, for example, a location and shape of a margin line of a prepared tooth is used in order to fabricate a crown or bridge. The margin line is typically located beneath the gingiva of a patient in the process of exposing the margin line in order to scan it with a structured light scanner or confocal scanner may be a painful and time-consuming process that involves packing the gingiva to push it away from the patient's tooth and then releasing the packing and quickly scanning the patient's tooth margin line before the gingiva collapses over the margin line. This process is painful to the patient and usually involves local anesthetic. FIG. 6 depicts a process for scanning a margin line using a multimodal scanner without packing the gingiva and without exposing the margin line.

At block 610 volumetric data of the intraoral cavity is generated using an OCT scanning process as described herein. At block 620 surface scan data is generated as described herein. For example, the volumetric data may be generated as described above with respect to at block 520 and surface scan data may be generated as discussed with respect to block 510. In some embodiments, the volumetric scan data and surface scan data may be positioned with respect to each other and a global coordinate system and a three-dimensional volumetric model of the patient's dentition may be generated. The three-dimensional volumetric model including both the surface scan data and volumetric data aligned with each other.

At block 630, the location and shape of the sub gingival margin line of the patient's prepared tooth may be determined from the volumetric data of the intraoral cavity. In some embodiments, the location and shape of the margin line of the patient's teeth may be extracted from the volumetric data of the intraoral cavity.

At block 640, the abutment or exposed surfaces of the patient's prepared tooth in the surface scan data may be combined with the sub gingival margin line data of the patient's prepared tooth in order to generate a three-dimensional model of the patient's prepared tooth including both the margin line and the abutment.

The three-dimensional model of the patient's prepared tooth including both the margin line in the abutment generated from the OCT data and the structured light data or confocal data may be used in order to generate a prosthetic such as a crown or bridge. In some embodiments, a similar method may be used in order to scan and determine the location of an implant and a patient's jaw. The sub gingival data from the OCT scan and the surface data from the structured light scan or confocal scan may be used in order to generate a model of the patient's dentition that includes a location and orientation of an implant. From this data abutment and prosthetic may be generated in order to restore the patient's dentition. In some embodiments, color data captured using the structured light system or confocal system may be used in order to match the color of the patient's prosthetic to the color of the patient's natural teeth. In some embodiments, OCT data may be used in order to determine the translucency of the patient's teeth so that the translucency of the patient's prosthetic may match the translucency of the patient's natural teeth. Sub-surface caries information may aid in removing caries by providing 3D volumetric data to aid in accurately drilling and removing the caries. Sub-surface gingiva data may be used in the treatment of gum recission.

Figure 7:
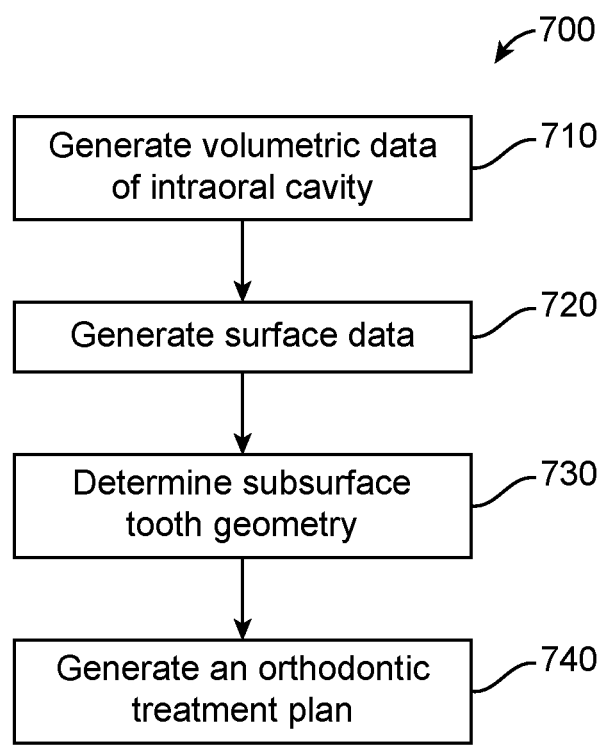
FIG. 7 shows a method of using multimodal scanning systems and methods in orthodontic treatment planning, in accordance with some embodiments.

With reference to FIG. 7, a method 700 of using a multimodal scanner in orthodontic treatment planning is shown. Orthodontic treatment planning is a process by which teeth are incrementally move from an initial position towards a final position in order to correct the malocclusion of a patient's teeth. In the treatment planning process in initial surface scan of the patient's teeth is generated and a final position of the patient's teeth is determined. Then movement paths to incrementally move the patient's teeth from the initial position towards the final position is generated and then orthodontic aligners are generated in fabricated and then worn by the patient in order to move their teeth. In a conventional scan only visible external surfaces of the patient's teeth are used to determine how the patient's teeth might move in response to orthodontic movement forces imparted by orthodontic aligners. FIG. 7 depicts a method for using subsurface information in order to create a more accurate model of the patient's tooth that may be used to more accurately determine how a patient's tooth might move in response to orthodontic movement forces.

At block 710 volumetric data of the intraoral cavity is generated using an OCT scanning process as described herein. At block 720 surface scan data is generated as described herein. For example, the volumetric data may be generated as described above with respect to at block 520 and surface scan data may be generated as discussed with respect to block 510. In some embodiments, the volumetric scan data and surface scan data may be positioned with respect to each other and a global coordinate system and a three-dimensional volumetric model of the patient's dentition may be generated. The three-dimensional volumetric model including both the surface scan data and volumetric data aligned with each other.

At block 730, the location and shape of the sub gingival hard tissues of the patient's teeth may be determined from the volumetric data of the intraoral cavity. In some embodiments the location and shape of the hard tissues of the patient's teeth may be extracted from the volumetric data of the intraoral cavity. In some embodiments, at block 730 the crown or exposed surfaces of the patient's teeth shown in the surface scan data may be combined with the sub gingival hard tissues of the patient's teeth in order to generate a three-dimensional model of the patient's teeth including both the crown portions of the patient's teeth and portions of corresponding roots of the patient's teeth.

At block 740 of the crown and root models of the patient's teeth may be used to generate an orthodontic treatment plan. In some embodiments, knowledge of the shape and location of the patient's root structure may aid in determining the forces and moments applied to the patient's teeth by orthodontic aligners in the teeth corresponding movements in reaction to those forces and moments. This knowledge may aid in generating more accurate predictions of the tooth movements and correspondingly more accurate and efficient treatment plans. The subsurface volumetric data may be used with the surface scan data to aid in detecting and locating caries, periodontitis, subgingival margin lines of prepared teeth, and oral cancer. In addition, subsurface root in information may be used to aid in determine whether to extract a tooth, for example, due to root issues, and subsurface, non-erupted teeth, may be imaged and such information and models may be used in treatment planning, such as to move erupted teach to make room for the non-erupted tooth.

Figure 8:
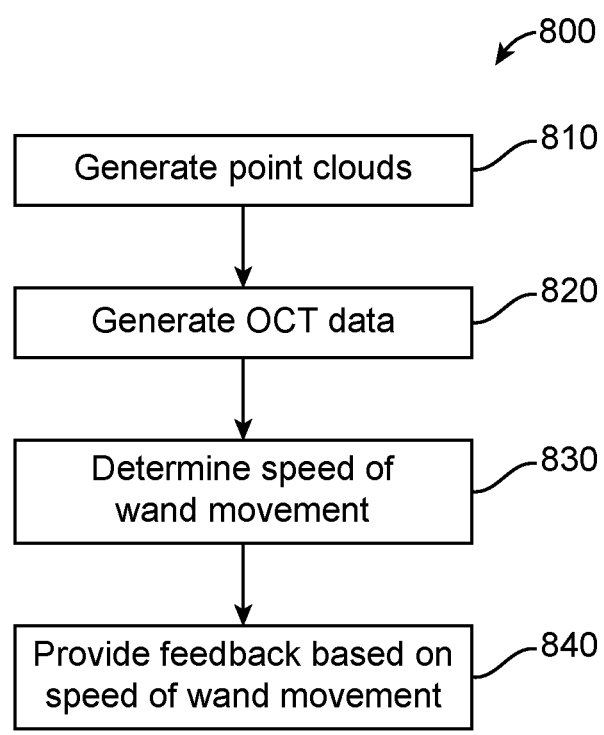
FIG. 8 shows a method of using multimodal scanning systems and methods to provide feedback to a user, in accordance with some embodiments.

In some embodiments, the process of generating an intraoral scan of the patient's dentition may include providing feedback to the operator of the scanner in order to guide the operator during the scanning process. For example, in some embodiments moving the scanning wand too quickly may result in poor scanning quality. Feedback provided to the operator may include an indication that the operator is moving the wand to quickly or a suggestion that the operator move the wand more slowly. FIG. 8 depicts a method 800 for providing feedback to an operator of the intraoral scanner. At block 810 point clouds are generated from the surface scan data and at block 820 subsurface OCT data is generated using an OCT scanning process. For example, the OCT scan data may be generated as described above with respect to at block 520 and surface scan data may be generated as discussed with respect to block 510. In some embodiments, the volumetric scan data and surface scan data may be positioned with respect to each other and a global coordinate system and a three-dimensional volumetric model of the patient's dentition may be generated. The three-dimensional volumetric model including both the surface scan data and volumetric data aligned with each other.

At block 830 the surface scan data and point clouds generated at block 810 may be used in order to determine a movement speed of the wand. The determined movement speed may be compared against one or more movement speed thresholds. For example, a first threshold may be a maximum movement speed for capturing OCT data and a second threshold may be a maximum movement speed for capturing structured light surface data or confocal surface data.

At block 840 feedback may be provided to the operator based on the comparison of determined movement speed and the one or more speed thresholds. For example, if OCT data is being captured, the feedback may indicate that the wand is moving too quickly for the capture accurate OCT data if the movement speed exceeds the maximum movement speed threshold for capturing OCT data. In some embodiments, the indication may be an instruction to the operator to slow down or an indication in the form of various colors based on exceeding one or more thresholds. In some embodiments, a first color such as green may indicate that the user is moving the wand below both the OCT and the structured light or confocal thresholds, while a second color, such as yellow may indicate that the operator has exceeded the maximum OCT scanning threshold, and third color, such as red may indicate that the operator has exceeded both the OCT and the structured light or confocal scanning thresholds. In some embodiments, the feedback may be a haptic feedback such as the vibration of the scanning wand when one or more thresholds or exceeded. In some embodiments, the feedback may include indications on the model of locations where data may be missing or additional scan data should be gathered. In some embodiments, the feedback may include indications on the model of locations where the scan data is sufficiently detailed for the desired use, such as caries detection or prosthetic generation.

Figure 9:
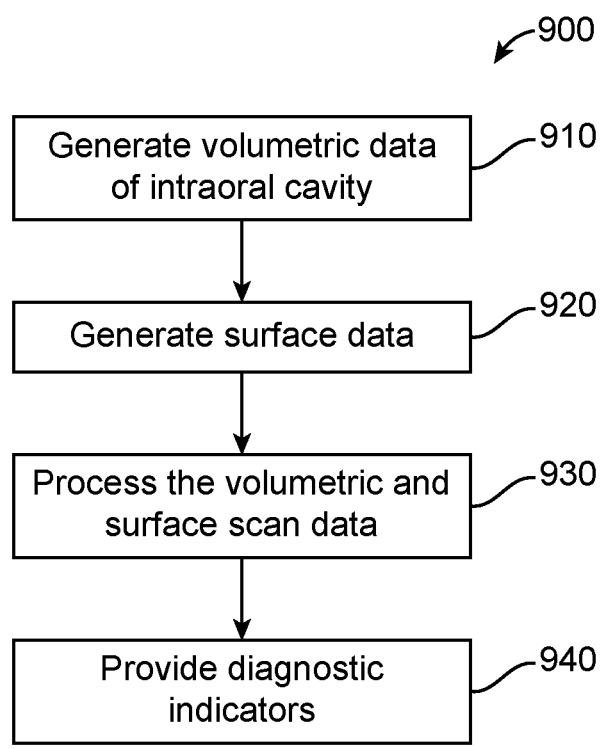
FIG. 9 shows a method of using multimodal scanning systems and methods for diagnosing and tracking lesions, in accordance with some embodiments.

With reference to FIG. 9, a method 900 of using a multimodal scanner to diagnose oral lesions is shown. At block 910 volumetric data of the intraoral cavity is generated using an OCT scanning process as described herein. At block 920 surface scan data is generated as described herein. For example, the volumetric data may be generated as described above with respect to at block 520 and surface scan data may be generated as discussed with respect to block 510. In some embodiments, the volumetric scan data and surface scan data may be positioned with respect to each other and a global coordinate system and a three-dimensional volumetric model of the patient's dentition may be generated. The three-dimensional volumetric model including both the surface scan data and volumetric data aligned with each other.

At block 930, the volumetric and surface scan data is process in order to determine the location and size of subsurface tooth lesions in the patient's dentition. For example, in some embodiments a machine learning algorithm trained using tagged models generated from previous scans of patient's teeth, may be used in order to find and classify lesions in the patient's dentition. The lesions may include caries, periodontal disease, oral cancer, and other types of lesions.

At block 940, diagnostic indicators, such as indicators for the location and type of lesions within the patient's dentition may be provided. For example, in some embodiments the indicators may be incorporated into the multimodal three-dimensional volumetric model of the patient's dentition. In some embodiments, the process 900 may be carried out over time such as at six-month intervals or during a patient's regular dental checkup. By carrying out the scanning and identification process 900 over time the patient's oral health may be tracked. Such tracking may lead to early identification and treatment of dental lesions.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions, such as a non-transitory computer readable medium. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A multimodal scanning system for scanning an intraoral object, the system comprising: an intraoral scanning wand having a distal end and a proximal end; a probe located at a distal end of the wand; a surface scanner located at a proximal end of the probe and configured to project light out of a distal end of the probe; and an OCT scanning system configured to project light out of the distal end of the probe.

Clause 2. The multimodal scanning system of clause 1, wherein the surface scanner is a structured light projector and wherein structured light projector and the OCT scanning system are in a known orientation with respect to each other.

Clause 3. The multimodal scanning system of clause 2, wherein the structured light projector and the OCT scanning system are coaxial with respect to each other.

Clause 4. The multimodal scanning system of clause 2, further comprising an imaging sensor.

Clause 5. The multimodal scanning system of clause 4, wherein the imaging sensor captures structured light reflected from the external surfaces of an intraoral object and OCT light reflected from the internal structure of the intraoral object.

Clause 6. The multimodal scanning system of clause 2, further comprising a control circuitry to drive the OCT scanning system and the structured light projector.

Clause 7. The multimodal scanning system of clause 4, further comprising a processor with memory containing instructions that when executed by the processor case the processor to generate a three-dimensional volumetric model of the intraoral object based on data generated by the structured light projector and the OCT scanning system.

Clause 8. The multimodal scanning system of clause 7, further comprising a scanning mirror configured to scan the OCT scanner in a scan pattern.

Clause 9. The multimodal scanning system of clause 8, wherein the scan pattern corresponds to a field of illumination of the structured light projector.

Clause 10. The multimodal scanning system of clause 2, wherein the OCT scanning system comprises a swept source.

Clause 11. The multimodal scanning system of clause 10, wherein the swept source sweeps over a range of wavelengths centered at about 1310 nm.

Clause 12. The multimodal scanning system of clause 10, wherein the swept source sweeps over a range of wavelengths between about 850 nm and about 1600 nm.

Clause 13. A method of multimodal scanning, the method comprising: generating surface scan data of an intraoral structure; generating volumetric scan data of an internal structure of the intraoral structure with OCT scanning; aligning the OCT scan data with the surface scan data; and generating a three-dimensional volumetric model of the patient's dentition based on the aligned OCT scan data and the surface scan data.

Clause 14. The method of multimodal scanning of clause 13, further comprising determining a position of a scanning wand during the generation of the surface scan data based on the surface scan data.

Clause 15. The method of multimodal scanning of clause 14, further comprising determining a position of the scanning wand during the generating of the volumetric scan data based on the position of the scanning wand during the generation of the surface scan data.

Clause 16. The method of multimodal scanning of clause 15, wherein generating volumetric scan data includes moving a field of illumination of an OCT scanning system in a scan pattern.

Clause 17. The method of multimodal scanning of clause 16, wherein the scan pattern corresponds to a field of illumination of a structured light projector.

Clause 18. The method of multimodal scanning of clause 13, further comprising correcting the volumetric scan data for diffraction effects based on the position of the wand with respect to the intraoral structure.

Clause 19. The method of multimodal scanning of clause 13, further comprising determining data of a shape of subgingival hard tissue.

Clause 20. The method of multimodal scanning of clause 19, further comprising generating an orthodontic treatment plan based on the surface scan data and the subgingival hard tissue.

Clause 21. The method of multimodal scanning of clause 20, further comprising combining the surface scan data with data of the shape of the subgingival hard tissue data.

Clause 22. The method of multimodal scanning of clause 21, wherein the subgingival hard tissue is tooth roots and the surface scan data includes tooth crowns.

Clause 23. The method of multimodal scanning of clause 19, further comprising generating a restorative treatment plan based on the surface scan data and the subgingival hard tissue.

Clause 24. The method of multimodal scanning of clause 23, further comprising combining the surface scan data with data of the shape of the subgingival hard tissue data.

Clause 25. The method of multimodal scanning of clause 24, wherein the subgingival hard tissue includes a margin line of a prepared tooth and the surface scan data includes a prepared tooth crown.

Clause 26. The method of multimodal scanning of clause 25, further comprising generating a prosthetic based on the combined surface scan data and the subgingival hard tissue data.

Clause 27. The method of multimodal scanning of clause 13, further comprising determining a movement speed of a scanning wand based on the surface scan data.

Clause 28. The method of multimodal scanning of clause 27, further comprising comparing the movement speed to a threshold and providing an indication based on the comparison of the movement speed with the threshold.

Clause 29. The method of multimodal scanning of clause 13, further comprising generating lesion data based on the three-dimensional volumetric model of the patient's dentition.

Clause 30. The method of multimodal scanning of clause 13, wherein generating lesion data based on the three-dimensional volumetric model of the patient's dentition includes using a machine learning algorithm trained on tagged three-dimensional volumetric models to determine the location of and classify the lesions.

Clause 31. The method of multimodal scanning of clause 30, further comprising providing diagnostic indicators based on the location and classification of the lesions.

Clause 32. The method of multimodal scanning of clause 31, wherein the lesions are one or more of caries, oral cancer, or periodontal disease.

Clause 33. A non-transitory computer readable medium, comprising instructions, that when executed by one or more processors, cause the one or more processors to carry out a method comprising: generating surface scan data of an intraoral structure; generating volumetric scan data of an internal structure of the intraoral structure with OCT scanning; aligning the OCT scan data with the surface scan data; and generating a three-dimensional volumetric model of the patient's dentition based on the aligned OCT scan data and the surface scan data.

Clause 34. The non-transitory computer readable medium of clause 33, wherein the instructions, that when executed by the one or more processors, further cause the one or more processors to carry out the method further comprising determining a position of a scanning wand during the generation of the surface scan data based on the surface scan data.

Clause 35. The non-transitory computer readable medium of clause 34, wherein the instructions, that when executed by the one or more processors, further cause the one or more processors to carry out the method further comprising determining a position of the scanning wand during the generating of the volumetric scan data based on the position of the scanning wand during the generation of the surface scan data.

Clause 36. The non-transitory computer readable medium of clause 35, wherein generating volumetric scan data includes moving a field of illumination of an OCT scanning system in a scan pattern.

Clause 37. The non-transitory computer readable medium of clause 36, wherein the scan pattern corresponds to a field of illumination of a structured light projector.

Clause 38. The non-transitory computer readable medium of clause 33, wherein the instructions, that when executed by the one or more processors, further cause the one or more processors to carry out the method further comprising correcting the volumetric scan data for diffraction effects based on the position of the wand with respect to the intraoral structure.

Clause 39. The non-transitory computer readable medium of clause 33, wherein the instructions, that when executed by the one or more processors, further cause the one or more processors to carry out the method further comprising determining data of a shape of subgingival hard tissue.

Clause 40. The non-transitory computer readable medium of clause 39, wherein the instructions, that when executed by the one or more processors, further cause the one or more processors to carry out the method further comprising generating an orthodontic treatment plan based on the surface scan data and the subgingival hard tissue.

Clause 41. The non-transitory computer readable medium of clause 40, wherein the instructions, that when executed by the one or more processors, further cause the one or more processors to carry out the method further comprising combining the surface scan data with data of the shape of the subgingival hard tissue data.

Clause 42. The non-transitory computer readable medium of clause 41, wherein the subgingival hard tissue is tooth roots and the surface scan data includes tooth crowns.

Clause 43. The non-transitory computer readable medium of clause 39, wherein the instructions, that when executed by the one or more processors, further cause the one or more processors to carry out the method further comprising generating a restorative treatment plan based on the surface scan data and the subgingival hard tissue.

Clause 44. The non-transitory computer readable medium of clause 43, wherein the instructions, that when executed by the one or more processors, further cause the one or more processors to carry out the method further comprising combining the surface scan data with data of the shape of the subgingival hard tissue data.

Clause 45. The non-transitory computer readable medium of clause 44, wherein the subgingival hard tissue includes a margin line of a prepared tooth and the surface scan data includes a prepared tooth crown.

Clause 46. The non-transitory computer readable medium of clause 45, wherein the instructions, that when executed by the one or more processors, further cause the one or more processors to carry out the method further comprising generating a prosthetic based on the combined surface scan data and the subgingival hard tissue data.

Clause 47. The non-transitory computer readable medium of clause 33, wherein the instructions, that when executed by the one or more processors, further cause the one or more processors to carry out the method further comprising determining a movement speed of a scanning wand based on the surface scan data.

Clause 48. The non-transitory computer readable medium of clause 47, wherein the instructions, that when executed by the one or more processors, further cause the one or more processors to carry out the method further comprising comparing the movement speed to a threshold and providing an indication based on the comparison of the movement speed with the threshold.

Clause 49. The non-transitory computer readable medium of clause 33, wherein the instructions, that when executed by the one or more processors, further cause the one or more processors to carry out the method further comprising generating lesion data based on the three-dimensional volumetric model of the patient's dentition.

Clause 50. The non-transitory computer readable medium of clause 33, wherein the instructions that when executed case the generating of the lesion data based on the three-dimensional volumetric model of the patient's dentition includes instructions for the method further comprising using a machine learning algorithm trained on tagged three-dimensional volumetric models of teeth to determine the location of and classify the lesions.

Clause 51. The non-transitory computer readable medium of clause 50, wherein the instructions, that when executed by the one or more processors, further cause the one or more processors to carry out the method further comprising providing diagnostic indicators based on the location and classification of the lesions.

Clause 52. The non-transitory computer readable medium of clause 51, wherein the lesions are one or more of caries, oral cancer, or periodontal disease.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A multimodal scanning system for scanning an intraoral object, the system comprising:
    an intraoral scanning wand having a distal end and a proximal end;
    a probe located at a distal end of the wand;
    a 3D surface scanner located at a proximal end of the probe and configured to project light out of a distal end of the probe and generate 3D surface data of the intraoral object;
    an OCT scanning system configured to project light out of the distal end of the probe; and
    a processor and memory comprising instructions that when executed cause the system to determine a location and orientation of the intraoral scanning wand with respect to the intraoral object based on the 3D surface data of the intraoral object, to determine a movement speed of the intraoral scanning wand based on 3D surface data of the intraoral object, compare the determined movement speed to a movement speed threshold for capturing OCT data, and provide feedback to a user when the movement speed exceeds the movement speed threshold.

2. The multimodal scanning system of claim 1, wherein the 3D surface scanner is a structured light projector and wherein structured light projector and the OCT scanning system are in a known orientation with respect to each other within the intraoral scanning wand.

3. The multimodal scanning system of claim 2, wherein the structured light projector and the OCT scanning system are coaxial with respect to each other.

4. The multimodal scanning system of claim 2, further comprising an imaging sensor.

5. The multimodal scanning system of claim 4, wherein the imaging sensor captures structured light reflected from the external surfaces of an intraoral object and OCT light reflected from the internal structure of the intraoral object.

6. The multimodal scanning system of claim 2, further comprising a control circuitry to drive the OCT scanning system and the structured light projector.

7. The multimodal scanning system of claim 4, wherein the instructions that when executed by the processor further cause the system to generate a three-dimensional volumetric model of the intraoral object based on data generated by the structured light projector and the OCT scanning system.

8. The multimodal scanning system of claim 7, further comprising a scanning mirror configured to scan the OCT scanner in a scan pattern.

9. The multimodal scanning system of claim 8, wherein the scan pattern corresponds to a field of illumination of the structured light projector.

10. The multimodal scanning system of claim 2, wherein the OCT scanning system comprises a swept source.

11. The multimodal scanning system of claim 10, wherein the swept source sweeps over a range of wavelengths centered at about 1310 nm.

12. The multimodal scanning system of claim 10, wherein the swept source sweeps over a range of wavelengths between about 850 nm and about 1600 nm.

13. A method of multimodal scanning, the method comprising:
    generating 3D surface scan data of an intraoral structure;
    generating volumetric scan data of an internal structure of the intraoral structure with OCT scanning;
    determining a location and orientation of the scanning wand during the generating of the volumetric scan data based on the position of the scanning wand during the generation of the 3D surface scan data;
    aligning the volumetric scan data with the 3D surface scan data based on the determined position and orientation;
    correcting the volumetric scan data for diffraction effects based on the position of the wand with respect to the intraoral structure; and generating a three-dimensional volumetric model of the patient's dentition based on the aligned and corrected volumetric scan data and the 3D surface scan data.

14. The method of multimodal scanning of claim 13, further comprising determining a position of the scanning wand during the generating of the volumetric scan data based on the position of the scanning wand during the generation of the 3D surface scan data.

15. The method of multimodal scanning of claim 14, wherein generating volumetric scan data includes moving a field of illumination of an OCT scanning system in a scan pattern.

16. The method of multimodal scanning of claim 15, wherein the scan pattern corresponds to a field of illumination of a structured light projector.

17. The method of multimodal scanning of claim 13, further comprising determining a shape of subgingival teeth roots based on the OCT scan data.

18. The method of multimodal scanning of claim 17, further comprising generating an orthodontic treatment plan based on the 3D surface scan data and the shape of the subgingival teeth roots.

19. The method of multimodal scanning of claim 13, wherein correcting the volumetric scan data for diffraction effects includes correcting the volumetric scan data for diffraction effects of varying tissue within the intraoral structure.

* * * * *